(12) United States Patent
Hale et al.

(10) Patent No.: US 6,500,982 B1
(45) Date of Patent: Dec. 31, 2002

(54) PROCESS FOR PREPARING (METH) ACRYLIC ACID

(75) Inventors: Timothy Allen Hale, Houston, TX (US); Robert Michael Mason, Houston, TX (US); Josefina Tseng Chapman, Norristown, PA (US); James Clarence Day, North Wales, PA (US); Chorng-Shyuan Tsay, Tao Yuan Hsien (TW)

(73) Assignee: Rohm and Haas Company, Philadelphia, PA (US)

( * ) Notice: Subject to any disclaimer, the term of this patent is extended or adjusted under 35 U.S.C. 154(b) by 130 days.

(21) Appl. No.: 09/593,631

(22) Filed: Jun. 13, 2000

Related U.S. Application Data

(60) Provisional application No. 60/141,534, filed on Jun. 28, 1999.

(51) Int. Cl.[7] .............................................. C07C 51/42
(52) U.S. Cl. ........................ 562/600; 562/532; 562/545
(58) Field of Search ........................... 562/532, 545, 562/600

(56) References Cited

U.S. PATENT DOCUMENTS

| | | | |
|---|---|---|---|
| 3,717,553 A | 2/1973 | Otsuki et al. | |
| 4,156,633 A | * 5/1979 | Horlenko et al. | ............ 562/600 |
| 4,203,906 A | 5/1980 | Takada et al. | |
| 4,256,783 A | 3/1981 | Takada et al. | |
| 4,365,087 A | 12/1982 | Kadowaki et al. | |
| 4,374,000 A | 2/1983 | Abernathy et al. | |
| 4,442,048 A | 4/1984 | Abernathy et al. | |
| 4,599,144 A | * 7/1986 | Baleiko et al. | ............. 562/600 |
| 4,780,568 A | * 10/1988 | Pascoe | ....................... 562/600 |
| 4,873,368 A | 10/1989 | Kadowaki et al. | |
| 5,161,605 A | 11/1992 | Gutlhuber | |
| 5,177,260 A | 1/1993 | Kawajiri et al. | |
| 5,198,578 A | 3/1993 | Etzkorn et al. | |
| 5,380,933 A | 1/1995 | Ushikubo et al. | |
| 5,426,221 A | * 6/1995 | Willersinn | ................... 562/600 |
| 5,504,247 A | * 4/1996 | Saxer et al. | ................. 562/600 |
| 5,637,222 A | * 6/1997 | Herbst et al. | ................ 210/634 |
| 5,728,872 A | * 3/1998 | Riemenschneide | .......... 562/598 |
| 5,739,391 A | 4/1998 | Ruppel et al. | |
| 5,785,821 A | 7/1998 | Sakamoto et al. | |
| 5,821,390 A | 10/1998 | Ruppel et al. | |

FOREIGN PATENT DOCUMENTS

| | | |
|---|---|---|
| EP | 0 695 736 | 2/1996 |
| EP | 0695736 A1 * | 2/1996 |
| EP | 0 765 856 | 4/1997 |
| EP | 0 856 343 | 8/1998 |
| EP | 0 911 313 | 4/1999 |

OTHER PUBLICATIONS

U.S. patent application Ser. No. 09/244,182.

* cited by examiner

Primary Examiner—Alan L. Rotman
Assistant Examiner—Taylor V. Oh
(74) Attorney, Agent, or Firm—Alan Holler

(57) ABSTRACT

This invention relates to a process for preparing (meth) acrylic acid, whereby turndown control is utilized to maintain optimal distillation column performance in the dehydration of aqueous (meth)acrylic acid to provide a (meth) acrylic acid solution.

20 Claims, 4 Drawing Sheets

PROCESS FOR PREPARING (METH) ACRYLIC ACID

This application claims the benefit of Provisional application No. 60/141,534, filed Jun. 28, 1999.

This invention relates to a process for preparing (meth) acrylic acid. In particular, the present invention relates to a process for preparing (meth)acrylic acid which utilizes turndown control to maintain optimal distillation column performance in the dehydration of aqueous (meth)acrylic acid to provide crude (meth)acrylic acid.

Acrylic acid is generally prepared by the vapor phase catalytic oxidation of at least one hydrocarbon material. For instance, acrylic acid may be prepared from propylene and/or acrolein in a one or two step process. In a first step propylene is oxidized in the presence of oxygen, diluent inert gasses, water vapor, and appropriate catalysts to produce acrolein according to equation (I):

$$C_3H_6 + O_2 \rightarrow C_2H_3CHO + H_2O + \text{heat} \qquad (I).$$

The acrolein is then oxidized, in a second step, in the presence of oxygen, diluent inert gasses, water vapor, and appropriate catalysts to form acrylic acid according to equation (II):

$$C_2H_3CHO + \tfrac{1}{2}O_2 \rightarrow C_2H_3COOH + \text{heat} \qquad (II).$$

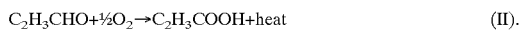

The acrolein may also be provided as starting material in a one step reaction (II) to produce acrylic acid.

Alternatively, propane may be used as a starting material. The propane is oxidized using appropriate catalysts, for instance, as described in U.S. Pat. No. 5,380,933 to form product acrylic acid.

Methacrylic acid is similarly prepared by the catalytic oxidation of isobutylene and/or isobutane.

The acrylic acid prepared using such vapor phase catalytic oxidation reactions is present in a mixed product gas exiting the reactor. Generally, the mixed product gas is cooled and is contacted with an aqueous stream in an absorption tower, thereby providing an aqueous acrylic acid solution which is then dehydrated in a distillation step to provide a crude acrylic acid stream. The crude acrylic acid stream can be used to produce various acrylic esters or be further purified to provide various grades of purified acrylic acid which can then be further utilized, for instance in the production of super absorbent polymer products or various other polymer materials.

Typically in the manufacture of acrylic acid there are instances wherein the aqueous acrylic acid feed rate to the distillation column and/or the aqueous acrylic acid feed stream composition fed to the distillation column changes. For instance, when the feed rate and/or composition of the aqueous acrylic acid feed stream is reduced below the maximum capacity of the system because of lower demand or as a result of variations in oxidation unit output. In a like manner, the feed rate of aqueous acrylic acid may increase as a result of increased demand or as a result of variations in the oxidation unit output. As a result, a changed amount or concentration of aqueous acrylic acid, is supplied to the distillation column, thereby leading to less or more aqueous acrylic acid being dehydrated in the distillation column and therefore the amount of crude acrylic acid produced is reduced or increased.

This can result in problems regarding maintaining optimal column performance, including adequate separation characteristics. Typically, at start up, a particular column is set to operate at a predetermined optimal vapor rate which is chosen to maintain suitable column performance. The optimal vapor rate is dependent on the distillation solvent to water ratio and distillation solvent feed rate for the system and is generally established by maintaining a predetermined distillation solvent to water ratio and distillation solvent feed rate. Also, a suitable amount of heat must be provided to the column to boil most of the distillation solvent and water overhead. Since it is generally assumed that the process will be operated at full capacity, an appropriate vapor rate is typically determined for optimal operation of the distillation column at or close to 100 percent of column capacity. Any changes from the predetermined capacity usage, i.e., changes in the aqueous acrylic acid feed or composition, may result in problems with the distillation column performance. For instance, when the feed rate of aqueous acrylic acid to a distillation column is reduced and the distillation solvent feed rate is held constant, the distillation column vapor rate is reduced and the distillation solvent to water ratio is increased. As a result, since the vapor rate is changed from its predetermined optimal value, column performance, including separation characteristics, suffers.

An additional problem may occur when product demand is reduced. Generally, if turndown control is unavailable, the manufacturer must completely shutdown to avoid excessive stockpiling of product acrylic acid which brings with it problems in storage, such as threat of polymerization, space usage and space availability. Furthermore, startup and shutdown procedures may be initiated more often.

As indicated above, the preparation and isolation of methacrylic acid proceeds by similar steps. Consequently, methacrylic acid manufacturers suffer from similar problems.

Distillation methods to remove water and impurities from aqueous (meth)acrylic acid solutions are know in the art. For instance, U.S. Pat. No. 5,785,821 discloses dehydration of an aqueous acrylic acid solution using a water insoluble solvent, e.g., toluene. The patent teaches wastewater recycle to the absorber of an acrylic acid process wherein the recycled wastewater stream has a specific composition of acetic acid (3–10 wt %), acrylic acid (0.5–5.0 wt%), and distillation solvent (0.01–0.5 wt%). Such a recycle stream, containing these specific amounts of acetic acid, acrylic acid and distillation solvent is said to enable collection of acrylic acid in the absorber at a high efficiency. However, this reference does not address the problem of distillation column turndown control in a process for preparing (meth) acrylic acid, which utilizes distillation to separate (meth) acrylic acid from water and impurities.

The present inventors have now discovered a process for preparing (meth)acrylic acid having turndown control in response to feed rate and/or composition changes in the aqueous (meth)acrylic acid stream fed to the distillation column. Such turndown control is achieved by controlling the amount of water or distillation solvent or both fed to the column to maintain a predetermined optimal vapor rate which provides optimal column performance. Furthermore, in one aspect, the invention enables obtaining additional value from process wastewater streams by utilizing such streams to adjust the water feed rate to the distillation column. This is done while maintaining suitable distillation column performance characteristics.

Accordingly, a novel process for preparing (meth)acrylic acid is described herein wherein the following advantages are provided:

(1) the ability to maintain column performance characteristics in response to feed rate and/or composition fluctuations in the aqueous (meth)acrylic acid fed to the distillation column, including the ability to avoid complete shutdown during low demand by running at reduced rates;

(2) additional value may be obtained from process wastewater streams by using them to adjust the water feed rate into the distillation column including recycling wastewater recovered from distillation column overheads directly for turndown control thereby reducing the wastewater load in the facility; and (3) reducing yield loss in the distillation column overheads by recycling wastewater recovered from distillation column overheads directly for turndown control.

In one aspect of the present invention, there is provided a process for preparing (meth)acrylic acid, including the steps of (A) feeding an aqueous (meth)acrylic acid stream including (meth)acrylic acid to a distillation column; (B) distilling the aqueous (meth)acrylic acid stream, at a predetermined vapor rate, in the presence of at least one distillation solvent substantially insoluble in water, to form a crude (meth) acrylic acid stream, and (C) maintaining the predetermined vapor rate in response to aqueous (meth)acrylic acid fluctuation by (i) monitoring a distillation solvent to water ratio during distillation and (ii) adjusting at least one of the amount of water and the amount of distillation solvent fed to the distillation column to maintain the predetermined vapor rate.

In a second aspect of the present invention, there is provided a process for preparing (meth)acrylic acid, including the steps of (A) feeding an aqueous (meth)acrylic acid stream including (meth)acrylic acid to a distillation column; (B) distilling the aqueous (meth)acrylic acid stream, at a predetermined vapor rate, in the presence of at least one distillation solvent, substantially insoluble in water, to form a crude (meth)acrylic acid stream, and (C) maintaining the predetermined vapor rate in response to aqueous (meth) acrylic acid fluctuation by (i) monitoring a distillation solvent to water ratio during distillation and (ii) adjusting the amount of water fed to the distillation column to maintain the predetermined vapor rate, wherein at least a portion of the adjusting amount of water includes recycled waste water.

In a third aspect of the present invention, there is provided a process for preparing (meth)acrylic acid, including the steps of (A) feeding an aqueous (meth)acrylic acid stream including (meth)acrylic acid to a distillation column; (B) distilling the aqueous (meth)acrylic acid stream, at a predetermined vapor rate, in the presence of at least one distillation solvent, to form a crude (meth)acrylic acid stream, and (C) maintaining the predetermined vapor rate in response to aqueous (meth)acrylic acid fluctuation by (i) monitoring a distillation solvent to water ratio during distillation and (ii) adjusting at least one of the amount of water and the amount of distillation solvent fed to the distillation column to maintain the predetermined vapor rate.

In a fourth aspect of the present invention, there is provided a process for preparing (meth)acrylic acid, including the steps of (A) feeding an aqueous (meth)acrylic acid stream including (meth)acrylic acid and at least one polymerization inhibitor selected from 4-hydroxy-2,2,6,6-tetramethyl-piperidinyloxy and derivatives thereof to a distillation column; (B) distilling the aqueous (meth)acrylic acid stream, at a predetermined vapor rate, in the presence of at least one distillation solvent, to form a crude (meth) acrylic acid stream, and (C) maintaining the predetermined vapor rate in response to aqueous (meth)acrylic acid fluctuation by (i) monitoring a distillation solvent to water ratio during distillation and (ii) adjusting at least one of the amount of water and the amount of distillation solvent fed to the distillation column to maintain the predetermined vapor rate.

Figure 1:
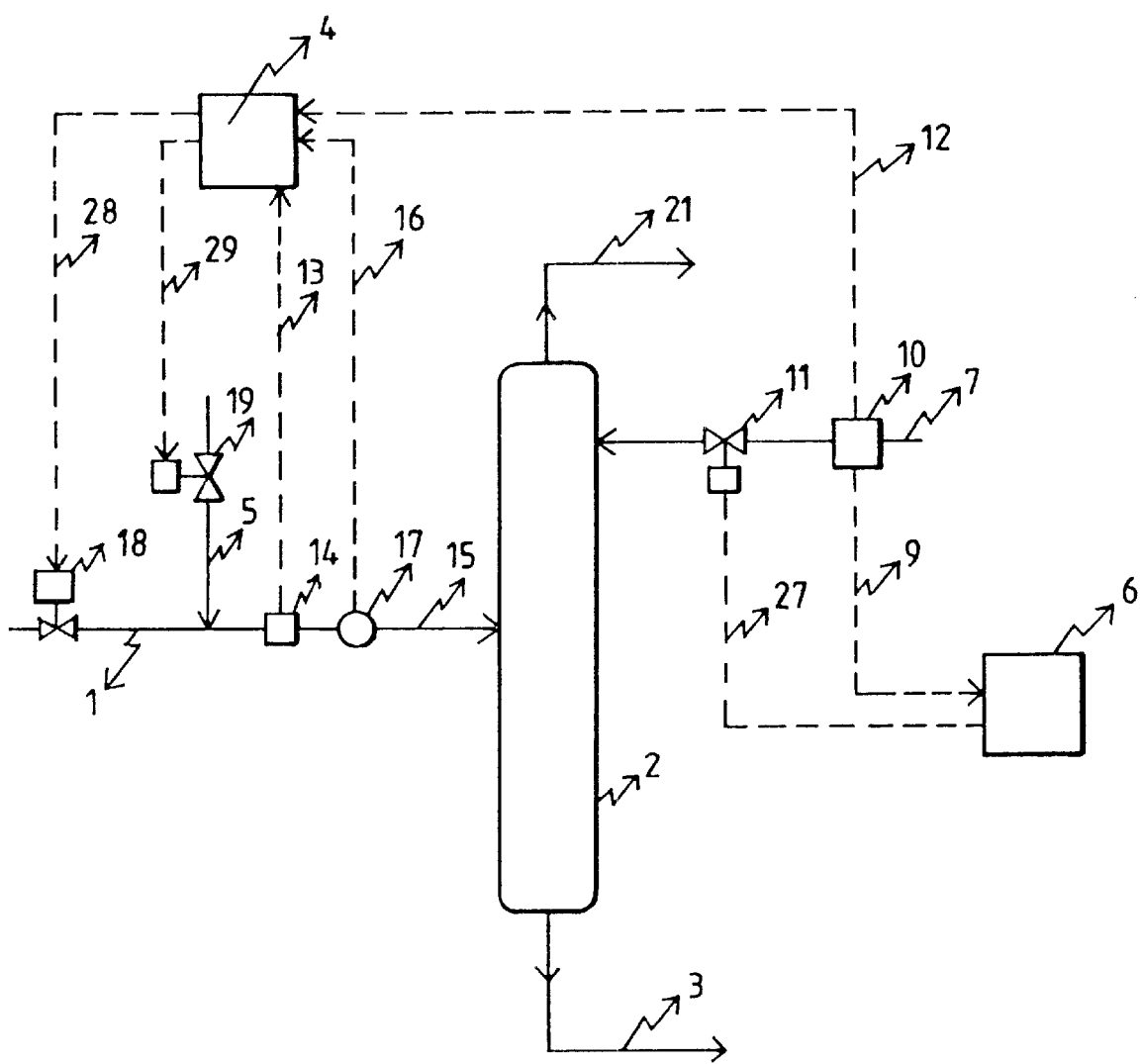
FIG. 1 depicts a (meth)acrylic acid process flow chart showing one embodiment of the process of the present invention.

Throughout this specification and claims, unless otherwise indicated, references to percentages are by weight percent and all temperatures are in degree centigrade.

It is also to be understood that for purposes of this specification and claims that the range and ratio limits, recited herein, are combinable. For example, if ranges of 1–20 and 5–15 are recited for a particular parameter, it is understood that ranges of 1–15 or 5–20 are also contemplated.

The term "wastewater" is understood to mean any water stream having impurities and/or additives contained therein.

The term "(meth)acrylic acid" is understood to encompass both acrylic acid and methacrylic acid and in a like manner the term (meth)acrylates is understood to encompass acrylates and methacrylates.

Also, the term "major amount" is understood to mean greater than 50 percent by weight of the total composition. The term "minor amount" is understood to mean less than 50 percent by weight of the total composition.

The term "turndown control", as used herein, is understood to encompass within its scope control in response to both lowering and raising of the aqueous (meth)acrylic acid feed and/or positive or negative changes to the composition of the aqueous acrylic acid stream fed to the distillation column.

The term "vapor rate" is understood to mean the flow rate of vapor in the distillation column. Such term is known in the art and as used herein is understood to have this generally accepted meaning.

The term "distillation solvent to water ratio", as used herein, is understood to mean the ratio of the total distillation solvent fed to the distillation column from any source and fed at any location to the column to the total water fed to the distillation column from any source and fed at any location to the column.

The term "aqueous (meth)acrylic acid fluctuation", as used herein is understood to include within its scope both change in the feed rate of aqueous (meth)acrylic acid to the distillation column and change in the composition of the aqueous (meth)acrylic acid stream fed to the distillation column.

The term "aqueous (meth)acrylic acid feed stream composition" as used herein is understood to mean the concentration of (meth)acrylic acid in the aqueous stream.

The process of the present invention will be initially described with reference to FIG. 1. Further reference to FIGS. 2, 3, and 4 will be made to describe various other embodiments of the invention. Also, although the present invention is described following in terms of a process for preparing acrylic acid, it is to be understood that the invention also encompasses a process for the preparation of methacrylic acid.

As recited above, the process of the present invention for preparing acrylic acid includes feeding an aqueous acrylic acid stream 1 formed by absorbing acrylic acid from a mixed product gas to a distillation column 2.

The mixed product gas is generally obtained by the vapor phase catalytic oxidation of a hydrocarbon material with a molecular oxygen containing gas in the presence of a suitable oxidation catalyst. The vapor phase catalytic oxidation of a hydrocarbon material to acrolein and/or acrylic acid, as well as reactors, catalysts, and processes for performing the same are generally known in the art and are described, for instance in U.S. Pat. Nos. 4,203,906; 4,256,783; 4,365,087; 4,873,368; 5,161,605; 5,177,260; 5,198,578; 5,739,391; 5,821,390, EP 911313, and co-pending U. S. patent application Ser. No. 09/244182.

Depending on the reactants fed to the reactor, the mixed product gas generally includes acrylic acid as well as inert gas(es), which include, but are not limited to, nitrogen, helium, argon, etc.; unreacted hydrocarbon reactants, which include, but are not limited to, propylene, acrolein, propane, isobutane, isobutylene, etc.; steam, and molecular oxygen containing reactants including, but not limited to, air, oxygen, etc.; reaction by-products including, but not limited to, acetic acid, formaldehyde, maleic acid, and other organics; as well as $CO_2$, CO and $H_2O$.

The mixed product gas is fed to an absorber wherein it is contacted with an aqueous stream thus producing aqueous acrylic acid stream 1. The aqueous acrylic acid stream 1 generally includes from 20 to 95, preferably 35 to 90, and more preferably 50 to 80 percent by weight acrylic acid; from 80 to 5, preferably from 65 to 10, more preferably from 50 to 20 percent by weight water; and up to 8, preferably up to 6, more preferably up to 5 percent by weight acetic acid.

As shown in FIG. 1, the aqueous acrylic acid stream 1 is fed to a distillation column 2 wherein it is subjected to distillation in the presence of at least one distillation solvent to form a crude acrylic acid stream 3. The crude acrylic acid stream 3 includes acrylic acid and may also include varying amounts of at least one of the following: water, acetic acid, propionic acid, β-acryloxypropionic acid (AOPA), acrolein, furfural, benzaldehyde, maleic acid, maleic anhydride, protoanemonin, acetaldehyde, and distillation solvent(s). The crude acrylic acid stream 3 generally includes from 90 to 99.9, preferably from 93 to 99.9, more preferably from 95 to 99.9 percent by weight acrylic acid. In one embodiment, the crude acrylic acid stream 3 is substantially free of water, i.e., has less than 1000, preferably less than 800, more preferably less than 500 ppm of water.

Figure 2:
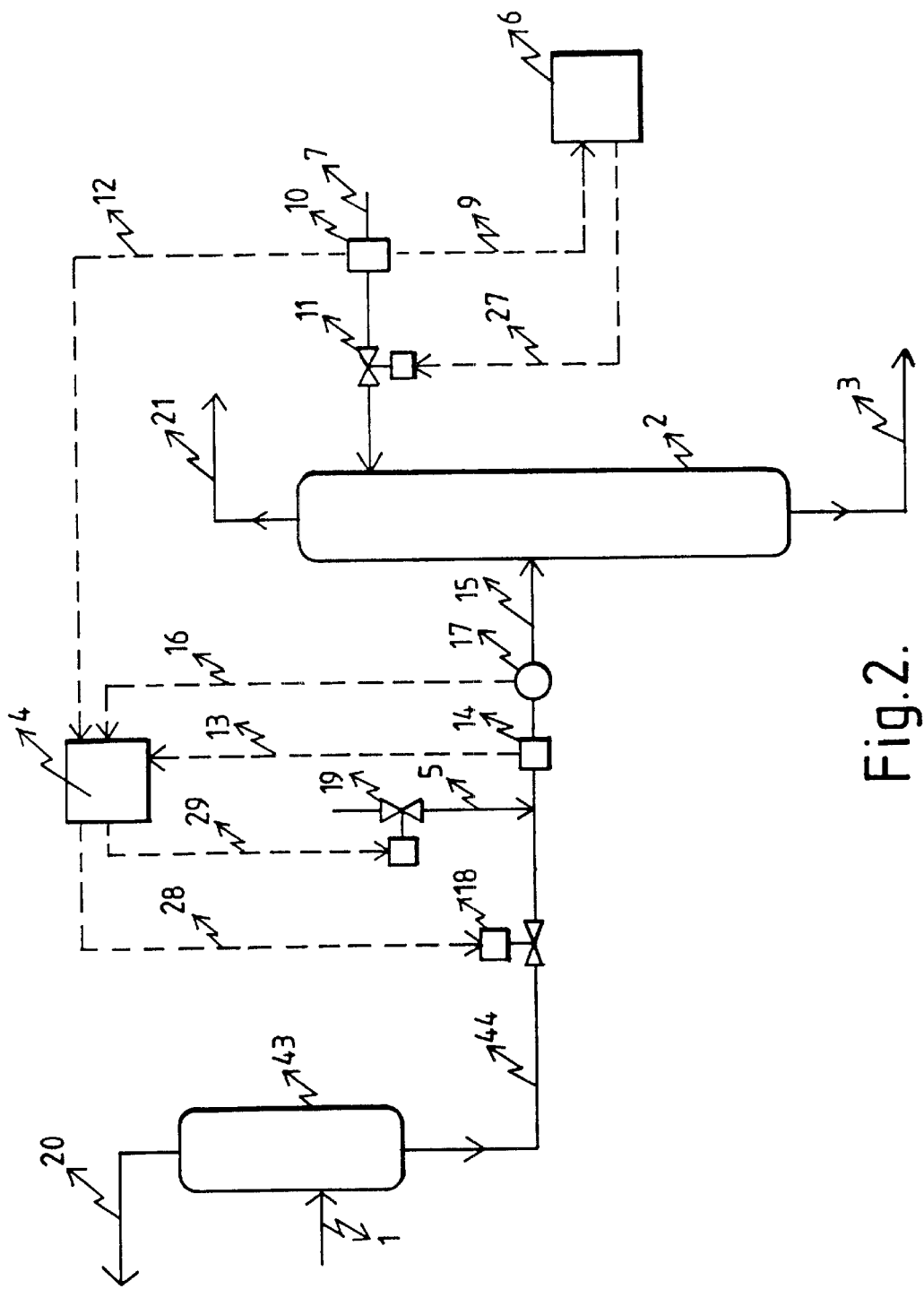
FIG. 2 depicts a (meth)acrylic acid process flow chart showing a second embodiment of the process of the present invention.

In one embodiment, as illustrated in FIG. 2, the aqueous acrylic acid stream 1 is fed to a light ends stripper column 43 before being fed to the distillation column 2. The light ends column 43 strips lights ends, including but not limited to, acrolein, formaldehyde, acetaldehyde, propionaldehyde, methyl ether, and methyl vinyl ketone, from the aqueous acrylic acid stream 1. Emerging from the bottom of the light ends column 43 is aqueous acrylic acid stream 44 which is substantially free of such light ends. Aqueous acrylic acid stream 44 generally has the same acrylic acid concentration recited above for aqueous acrylic acid stream 1. Aqueous acrylic acid stream 44 is then introduced into the distillation column 2. The stream 20 emerging from the top of the light ends column 43 is sent to waste or recycled back to the absorbing operation wherein some of the stripped acrolein is recovered in the absorber off gas and recycled back to the oxidation reactor thereby improving the yield of acrylic acid.

The aqueous acrylic acid streams 1 or 44 may also be treated with a basic compound such as, but not limited to, sodium hydroxide, potassium hydroxide, or calcium carbonate to react out maleic acid impurities. The basic compound is added at a stoichiometric ratio to the maleic acid impurity.

Other additives such as oxazolidine derivatives may be added to the aqueous acrylic acid to reduce the level of aldehydes present in the crude acrylic acid product.

Any distillation methods known in the art may be utilized, including but not limited to, simple distillation, multi-stage distillation, azeotropic distillation, and steam distillation. In addition, the distillation column may be any suitable distillation column known in the art. Suitable examples include, but are not limited to, sieve tray, dual flow tray, or packed distillation columns. In one embodiment, azeotropic distillation is utilized. In another embodiment, a dual flow tray design is utilized. Weep holes may also be provided for in the distillation column design for the removal of polymerizable liquids, e.g., acrylic acid, from the trays. The polymerizable liquids may collect on the trays of the distillation column and tend to polymerize, thus requiring more frequent shutdown to clean the column of polymeric materials. Such weep holes are known in the art and are described for instance in U.S. Pat. Nos. 4,442,048; 4,374,000; 3,717,553; and EP 856343. In one embodiment, a dual flow tray distillation column is utilized having weep holes.

The distillation solvent or solvents may be any solvent(s) suitable for the distillation of an acrylic acid stream. Suitable examples of distillation solvent useful in the present invention include, but are not limited to, ethyl acetate, butyl acetate, dibutyl ether, ethyl acrylate, methyl methacrylate, ethyl methacrylate, diethyl ketone, methyl propyl ketone, methyl isobutyl ketone, methyl tert-butyl ketone, isopropyl acetate, n-propyl acetate, heptane, heptene, cycloheptane, cycloheptene, cycloheptadiene, cycloheptatriene, methylcyclohexane, ethylcyclopentane, dimethylcyclohexane, ethylcyclohexane, toluene, ethylbenzene, xylene, trichloroethylene, trichloropropene, dichlorobutane, chloropentane, chlorohexane, chlorobenzene, and mixtures thereof. In one embodiment, the distillation solvent is substantially water insoluble, generally having a solubility in water at room temperature of 0.5 weight percent or less, preferably 0.2 weight percent or less. Suitable examples of such a water insoluble distillation solvent include, but are not limited to, heptane, heptene, cycloheptane, cycloheptene, cycloheptadiene, cycloheptatriene, methylcyclohexane, ethylcyclopentane, dimethylcyclohexane, ethylcyclohexane, toluene, ethylbenzene, xylene, trichloroethylene, trichloropropene, dichlorobutane, chloropentane, chlorohexane, chlorobenzene, and mixtures thereof. In an alternative embodiment, the distillation solvent is a mixed solvent which includes at least two solvents. Suitable examples of solvents useful in such mixed solvent include, but are not limited to, diethyl ketone, methyl propyl ketone, methyl isobutyl ketone, methyl tert-butyl ketone, isopropyl acetate, n-propyl acetate, toluene, heptane and methylcyclohexane. The preferred distillation solvent is toluene.

The distillation solvent may be entirely fed to the top tray of the distillation solvent or alternatively may be fed to the column at various points simultaneously.

As indicated above, the process of the present invention features turndown control of the distillation column which compensates for fluctuations in the feed rate and/or composition of aqueous acrylic acid fed to the distillation column 2 so that column performance, including separation characteristics, remain at optimal levels. Generally, distillation column 2 performance is optimized in response to fluctuations in the aqueous feed rate and/or composition by monitoring the distillation solvent to water ratio and adjusting the water and/or distillation solvent feed to the distillation column 2 to maintain a predetermined value for the vapor rate.

In one embodiment, as described in FIG. 1, turndown control of the distillation column 2 is achieved as follows. A distillation solvent feed rate controller 6 which controls the distillation solvent feed stream 7 is set at a predetermined rate at process start up. A distillation solvent to water ratio controller 4 controlling makeup water stream 5 and aqueous acrylic acid feed stream 1 is set, at process start up, at a predetermined distillation solvent to water ratio. Makeup water stream 5 and acrylic acid feed stream 1 combine to form total aqueous acrylic acid feed stream 15. Once the distillation solvent to water ratio and distillation solvent feed rate are set, the column vapor rate is fixed at an optimal, predetermined value that gives good column performance. Typically, good column performance is evidenced by good separation, product produced which is within specifications, and minimal yield loss in the column distillate streams. Generally, the goal is to maintain a constant vapor rate and the appropriate overhead vapor composition, e.g., if azeotropic distillation is used an appropriate azeotrope composition.

For purposes of describing this embodiment it is assumed that the distillation solvent feed rate and the distillation solvent to water ratio of the distillation column 2 are set to run at maximum feed rates, i.e., 100 percent capacity, so that predominantly all of the water requirements of the distillation column 2 at start up are provided by the aqueous acrylic acid feed stream 1. However, makeup water stream 5 is also utilized to control minor variations in the aqueous acrylic acid feed stream 1, which are not associated with deliberate turndown or major fluctuations of the system.

Once the distillation solvent to water ratio and distillation solvent feed rate are set at start up to optimal values, the internal vapor flow, i.e., vapor rate, of the distillation column is set. Setting of the predetermined values will vary according to the type of distillation column utilized and of course will account for the capacity utilization of the column. For example, if a dual flow tray column is utilized, for good dual flow tray performance the distillation solvent to water ratio and distillation solvent feed rate are set to promote a good, constant vapor rate through the trays at a particular capacity usage. Determination of the preset values of the distillation solvent to water ratio and distillation solvent feed rate is within the abilities of those skilled in the art and is not discussed further herein.

In this embodiment, the distillation solvent feed rate is controlled by a simple flow control loop. As indicated, the distillation solvent feed rate controller 6 is set at a predetermined distillation solvent feed rate. The distillation solvent feed rate controller 6 monitors a signal 9 which it receives from distillation solvent feed stream flow meter 10 regarding the flow rate of distillation solvent feed stream 7. The distillation solvent feed rate controller 6 determines whether an adjustment in the flow rate of distillation solvent feed stream 7 is needed to maintain the predetermined distillation solvent feed rate and signals 27 the distillation solvent control valve 11 accordingly. In this embodiment, the aforementioned control loop is mainly utilized to correct for minor fluctuations in the distillation solvent feed stream 7 so as to maintain a constant distillation solvent feed rate.

Control of the distillation solvent to water ratio is more complex in this embodiment. As indicated above, the distillation solvent to water ratio controller 4 is set to maintain a predetermined vapor rate. The distillation solvent to water ratio controller 4 receives:

(1) a signal 12 from the distillation solvent feed stream flow meter 10 regarding the flow rate of distillation solvent feed stream 7;

(2) a signal 13 from the total aqueous acrylic acid feed flow meter 14 regarding the flow rate of total aqueous acrylic acid feed stream 15; and (3) a signal 16 from water composition meter 17 regarding the water composition of total aqueous acrylic acid feed stream 15.

In response to signals 12, 13, and 16 the distillation solvent to water ratio controller 4 determines whether an adjustment in the flow rate of aqueous acrylic acid feed stream 1 and/or the makeup water stream 5 is needed to maintain the predetermined vapor rate and signals the aqueous acrylic acid feed stream control valve 18 (signal 28) and/or the makeup water feed stream control valve 19 (signal 29) accordingly.

It will be understood by those skilled in the art that the distillation solvent to water ratio controller 4 may directly control aqueous acrylic acid feed stream control valve 18 and/or the makeup water feed stream control valve 19 or may indirectly control them by sending signals 28 and/or 29 as set-points to independent flow controllers. Such independent loops may be, for instance, a flow control loop as described above for control of the distillation solvent feed stream 7 into the distillation column 2. In such a case, the distillation solvent to water ratio controller 4 would send signals 28 and/or 29 to the independent controllers which would then adjust the acrylic acid feed stream control valve 18 and/or the makeup water feed stream control valve 19 (signal 29) accordingly to provide the appropriate water flow into the distillation column 2.

Chemical process controllers, flow meters, and composition meters are known in the art and any suitable controller and meter may utilized in the present invention. Suitable chemical process controllers include, but are not limited to, proportional (P) controllers, proportional plus integral (P-I) controllers, proportional plus derivative (P-D) controllers, proportional plus integral plus derivative (P-I-D-) controllers, and fuzzy logic and neural network controllers. Suitable flow meters include, but not limited to, Dahl flow tube, Kennison flow nozzle, pitot tube, pitot-static tube, venturi meter, ultrasound, turbine, and orifice flow meter. Suitable composition meters include, but are not limited to, sound velocity meter, ultraviolet analyzer, infrared analyzer, mass spectrometer, X-ray absorption, hydrostatic, and the like.

While the present invention is described in terms of adjusting the water content of the total aqueous acrylic acid feed stream 15, it will be understood by those skilled in the art that a number of system parameters may be adjusted to maintain the predetermined vapor rate. For instance, instead of adjusting the amount of water fed to the distillation column, the amount of distillation solvent fed to the distillation column 2, the crude acrylic acid production rate, the aqueous strength of aqueous acrylic acid streams 1 or 44, manipulating both the water and distillation solvent feed amounts to distillation column 2 and/or any combination thereof may be adjusted to maintain the required vapor rates.

The water in makeup water stream 5 may be from any suitable source, including city water, deionized (DI) water and wastewater or mixtures thereof. In one embodiment the water is DI water. In one embodiment, at least a portion of the makeup water stream 5 is recycled wastewater. The wastewater may be any wastewater suitable for use in an acrylic acid dehydration operation and may be from any source. Consequently, it is not necessary that the wastewater be derived from the same process into which it is recycled. For instance, the wastewater may be derived from one (meth)acrylic acid process and recycled into another. Suitable examples of wastewater include, but are not limited to, wastewater derived from dehydration of (meth)acrylic acid, other aqueous distillates, steam condensates and raffinates. In a like manner, it is not necessary that the wastewater be derived from a (meth)acrylic acid wastewater stream. Accordingly, the wastewater may be derived from other chemical process wastewater streams, for example, from a (meth)acrylate process stream. Furthermore, the wastewater may be derived from a natural source such as a river, well, spring or the like.

The makeup water stream 5 may include any suitable amount of recycled waste water, i.e., from 0 to 100 weight percent recycled wastewater. Typically, the makeup water stream 5 will be a mixture of a recycled wastewater stream from an acrylic acid manufacturing process and an essentially pure water stream, e.g., deionized water. In one embodiment, the makeup water stream 5 includes a major amount of wastewater. In another embodiment, the makeup water stream 5 includes from 0.1 percent by weight to 100 percent by weight of wastewater. Preferably, the makeup water stream 5 contains 100 percent by weight wastewater. Regardless of how much recycled wastewater is utilized, the makeup water stream 5 will contain a major amount of water and minor amounts of impurities derived from a (meth) acrylic acid and/or (meth)acrylate manufacturing process. In another embodiment, the aqueous stream is substantially free of distillation solvent(s).

Figure 3:
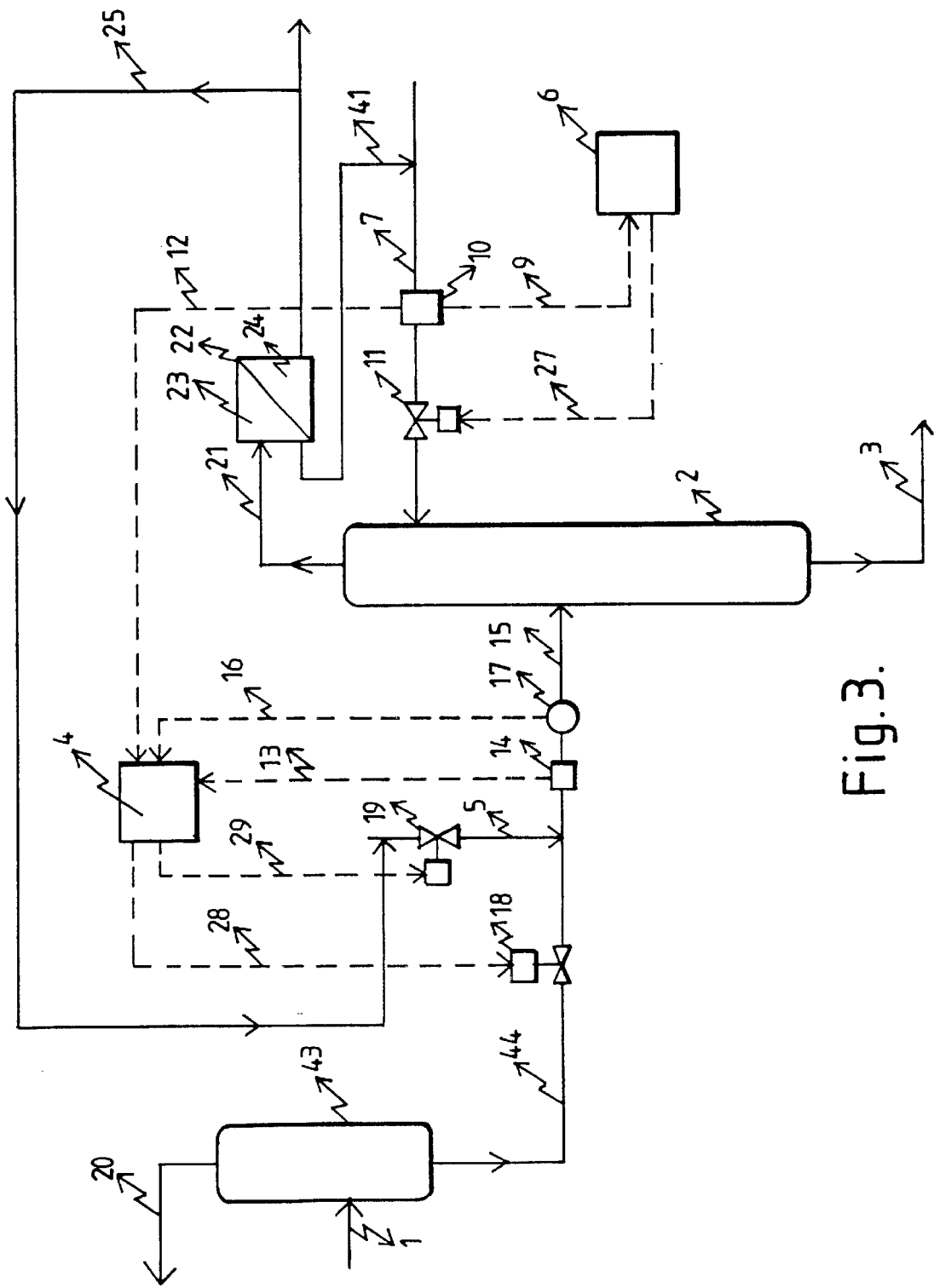
FIG. 3 depicts a (meth)acrylic acid process flow chart showing a third embodiment of the process of the present invention.

In one embodiment, shown in FIG. 3, at least a portion of the makeup water stream 5 is a recycle wastewater stream derived from the overhead vapor stream 21 emanating from the top of the distillation column 2. The overhead vapor stream 21 generally includes, but is not limited to, water, acrylic acid, acetic acid and/or distillation solvent. The overhead vapor stream 21 is condensed and phase separated into organic and aqueous phases. The phase separation may be done by any means known in the art.

In the embodiment of FIG. 3, the overhead vapor stream 21 is condensed and introduced into a phase separation tank 22 and allowed to phase separate into an organic phase 23 and an aqueous phase 24. The organic phase 23 predominantly includes the distillation solvent. The aqueous phase 24 includes, but is not limited to, acrylic acid, acetic acid, the distillation solvent and water. In this embodiment, at least a portion of the aqueous phase 24 is recycled 25 to makeup water stream 5 for use in turndown control. As indicated above, it is to be understood that the aqueous phase 24 may be recycled, in part or completely, to the makeup water stream 5.

If distillation solvents having a higher solubility in water are utilized, direct recycle of the aqueous phase 24 back to makeup water stream 5 may become disadvantageous because the aqueous phase 24 will contain a larger amount of distillation solvent. In such a case, an increased amount of distillation solvent will be returned to the bottom portion of the distillation column 2. Consequently, this will result in an unwanted increase in the amount of distillation solvent appearing in the dehydrated acrylic acid. Consequently, before recycle the concentration of distillation solvent in the aqueous phase 24 at times must be lowered. This may be done by any number of methods know in the art, for instance, by dilution with an aqueous stream having less or no distillation solvent or by processing methods such as use of a stripping column or the like.

Figure 4:
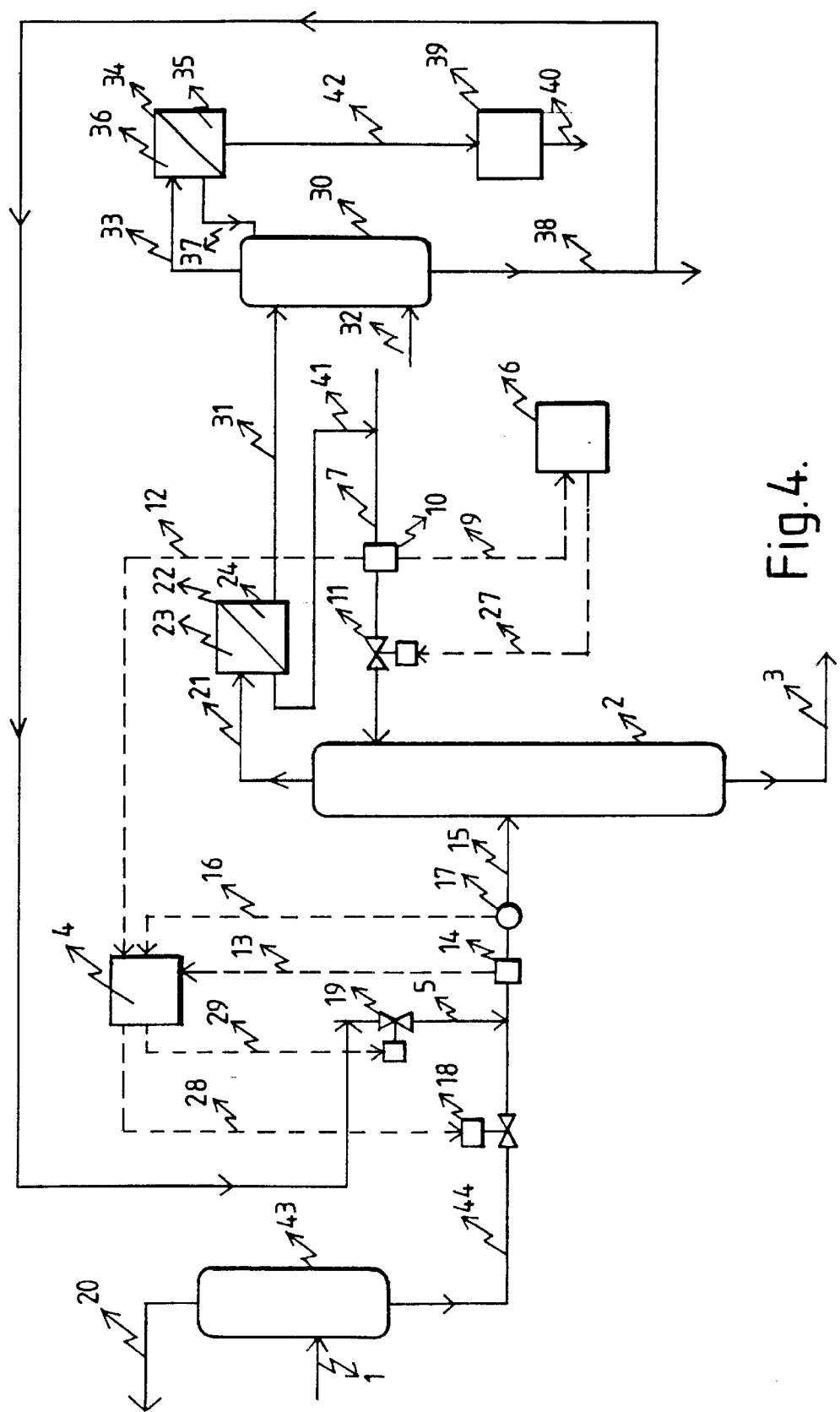
FIG. 4 depicts a (meth)acrylic acid process flow chart showing a fourth embodiment of the process of the present invention.

In one embodiment of the present invention, as illustrated by FIG. 4, this problem is addressed. A raffinate stripper 30 may be used to strip distillation solvent from the aqueous phase 24. The raffinate stripper 30 may be any stripping column known in the art. The raffinate stripper 30 receives the aqueous phase 24 from the tank 22 through feed 31 and strips the distillation solvent from the aqueous phase 24 using a stripping gas 32. The stripping gas 32 may be generated by the contents of a reboiler attached to the stripping column or may be steam from any source. The raffinate stripper typically operates at a temperature of from 80° C. to 120° C. and at atmospheric pressure. Preferably, the raffinate stripper operates at a temperature of from 95° C. to 110° C. The overhead vapor stream 33 is condensed and introduced into a tank 34 and allowed to phase separate into an organic phase 35 and an aqueous phase 36. The organic phase 35 predominantly includes the stripped distillation solvent. The aqueous phase 36 includes wastewater substantially free of distillation solvent. In this embodiment, at least a portion of the aqueous phase 36 is recycled 37 back to the stripping column 30 or be recycled for other use or be sent to waste. From the bottom of stripping column 30 emanates a wastewater stream 38 at least a portion of which is recycled to makeup water stream 5. Alternatively, some of wastewater stream 38 may be recycled for other use or be sent to waste. For instance, the waste water stream may be used as a water feed in absorbers for different acrylic acid production units, or as indicated as all or a portion of makeup water stream 5, or may be disposed of in a waste water treatment plant. The organic phase 35 is sent, through feed 42, to a recycle solvent tank 39 which may be used to generate new inhibitor feed streams or be recycled 40 to distillation solvent feed stream 7.

The organic phase 23 may also be recycled 41 back to the distillation column by way of the distillation solvent feed stream 7 so that the distillation solvent may be reused or organic phase 23 may be used to form an inhibitor makeup stream to facilitate feeding polymerization inhibitor to the distillation column.

In a further embodiment, the aqueous acrylic acid stream 1 or 44 includes at least one polymerization inhibitor. Suitable inhibitors include, but are not limited to, hydroquinone; para-benzoquinone; phenothiazine. 4-methoxy phenol; 4-ethoxyphenol; 1,2-dihydroxybenzene; catechol monobutyl ether; pyrogallol; 4-aminophenol; 2-mercaptophenol; 4-mercaptophenol; 4-hydroxy-2,2,6,6-tetramethylpiperidinyloxy, free radical; 4-oxo-2,2,6,6-tetramethylpiperidinyloxy, free radical; 4-amino-2,2,6,6-tetramethylpiperidinyloxy, free radical; 4-propoxyphenol; 4-butoxyphenol; 4-heptoxyphenol; hydroquinone monobenzylether; 1,2-dihydroxybenzene; 2-methoxyphenol; 2,5-dichlorhydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 2-aminophenol; 2-N,N-dimethylaminophenol; 4-ethylaminophenol; 2,3-dihydroxyacetophenone; 1,2-dimethylether; 2-methylthiophenol; t-butyl catechol; di-tert-butylnitroxide; di-tert-amylnitroxide; 2,2,6,6-tetramethylpiperidinyloxy; 4-dimethylamino 2,2,6,6-tetramethyl-piperidinyloxy; 4-amino-2,2,6,6-tetramethyl-piperidinyloxy; 4-ethanoyloxy-2,2,6,6-tetramethylpiperidinyloxy; 2,2,5,5-tetramethyl-pyrrolidinyloxy; 3-amino-2,2,5,5-tetramethylpyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; copper compounds such as copper dimethyldithiocarbamate; copper diethyldithiocarbamate; copper salicylate; isomers thereof; derivatives thereof; mixtures of two or more thereof; or mixtures of one or more of the above with molecular oxygen. In one embodiment, the polymerization inibitor is 4-hydroxy-2,2,6,6-tetramethyl-piperidinyloxy, derivatives thereof or mixtures of 4-hydroxy-2,2,6,6-tetramethyl-piperidinyloxy with molecular oxygen.

In an alternative embodiment, the polymerization inhibitor is a mixture of 4-hydroxy-2,2,6,6-tetramethyl-piperidinyloxy, derivatives thereof or mixtures of 4-hydroxy-2,2,6,6-tetramethyl-piperidinyloxy with hydroquinone and molecular oxygen.

Should a distillation column design which requires use of a vapor phase polymerization inhibitor be used, such as a sieve tray, suitable vapor phase inhibitors include N-nitrosophenylhydroxylamine and salts thereof.

The acrylic acid stream 3 is generally sent to be used as a raw material in acrylic ester or acrylate polymer production. The acrylic acid may be used as is or be further processed to purer grades of acrylic acid before use.

The following Examples are provided as an illustration of the present invention.

EXAMPLE 1

Azeotropic Distillation with Toluene Solvent at 100% Capacity

An extended run of an azeotropic toluene distillation column was conducted at operating conditions using a 1 inch diameter, 30-tray Oldershaw column mounted on a bottoms reboiler pot sparged with air at a rate of 30 cc/min. The feed tray was at tray 15 and the control tray was at tray 18, both from the bottom. The distillation was operated at the following conditions:

215 mm Hg top pressure
155 g/hr aqueous AA feed rate
333 g/hr toluene reflux rate
75° C. control tray temperature An aqueous acrylic acid feed composition was fed to the distillation column at tray 15 and toluene reflux was fed to the top tray at the rate indicated. The aqueous acrylic acid feed composition contained 67 wt. % acrylic acid, 1 wt. % β-acryloxypropionic acid (AOPA), 28 wt. % water, and 3 wt. % acetic acid, and 1 wt. % other minor components such as formaldehyde, formic acid, maleic acid, and hydroquinone polymerization inhibitor. The hydroquinone was available from Aldrich Chemical Co. of Milwaukee, Wis. Also, a 0.08 wt. % aqueous solution of 4-hydroxy-2,2,6,6-tetramethyl piperidinyloxy, free radical polymerization inhibitor, available from Aldrich Chemical Co. of Milwaukee, Wis., was fed into the aqueous acrylic acid feed at a rate of 5 g/hr and 0.24 wt. % aqueous solution of p-benzoquinone vapor phase inhibitor, available from Aldrich Chemical Co. of Milwaukee, Wis., was fed to the top tray at a rate of 10 g/hr. Furthermore, an additional stream of 0.34 wt. % aqueous solution of 4-hydroxy-2,2,6,6-tetramethyl piperidinyloxy, free radical was fed to the top tray at a rate of 5 g/hr. The inhibitor feeds resulted in inhibitor levels in the column, based on bottoms, of 200 ppm of 4-hydroxy-2,2,6,6-tetramethylpiperidinyloxy, free radical, 316 ppm hydroquinone, and 650 ppm of p-benzoquinone.

The distillation ran smoothly for 99 hours. At the end of the run, the column and pot were clean, i.e., no polymerization of monomer was detected. Analysis by gas chromatography showed that the effluent streams had the following compositions:

Bottoms (105.7 g/hr):
96 wt. % AA
4 wt. % AOPA
280 ppm HAc
0.2 ppm toluene

Aqueous distillate (54.3 g/hr):
91.0 wt. % H2O
1.6 wt. % AA
7.4 wt. % HAc
393 ppm toluene The acrylic acid yield loss through the aqueous distillate was 0.82%.

EXAMPLE 2

Azeotropic Distillation with Toluene Solvent at 50% Turndown

An extended azeotropic distillation was run as described in Example 1.

The distillation was turndown to run at a 50% turndown rate, i.e., at 50% aqueous feed rate. A calculated amount of DI water was added to the aqueous feed as make-up water so as to maintain the desired vapor rate. The operating conditions were as follows:

215 mm Hg top pressure
77.5 g/hr aqueous AA feed rate
22.9 g/hr DI water feed rate
300 g/hr toluene reflux rate
67° C. control tray temperature An aqueous acrylic acid feed composition, with added DI water, was fed to the distillation column at tray 15 and toluene reflux was fed to the top tray at the rates indicated. The aqueous acrylic acid feed composition contained 67 wt.% acrylic acid, 1 wt. % β-acryloxypropionic acid (AOPA), 28 wt. % water, and 3 wt.% acetic acid, and 1 wt. % other minor components such as formaldehyde, formic acid, maleic acid, and hydroquinone polymerization inhibitor. The hydroquinone was available from Aldrich Chemical Co. of Milwaukee, Wis. Also, 4-hydroxy-2,2,6,6-tetramethylpiperidinyloxy, free radical polymerization inhibitor, available from Aldrich Chemical Co. of Milwaukee, Wis., was fed as a 0.13 wt. % aqueous solution into the aqueous acrylic acid feed at a rate of 5 g/hr and p-benzoquinone vapor phase inhibitor, available from Aldrich Chemical Co. of Milwaukee, Wis., as a 0.12 wt. % toluene solution and an additional stream of 4-hydroxy-2,2,6,6-tetramethylpiperidinyloxy, free radical as a 0.26 wt.% toluene solution were fed to the top tray at a rate of 10 g/hr. The inhibitor feeds resulted in inhibitor levels in the column, based on bottoms, of 200 ppm of 4-hydroxy-2,2,6,6-tetramethylpiperidinyloxy, free radical, 316 ppm hydroquinone, and 650 ppm of p-benzoquinone.

The experiment ran smoothly for 18 hours. At the end of the run, the column and pot were clean, i.e., no monomer polymerization and the effluent streams had the following compositions:

Bottoms (52.6 g/hr):
96 wt. % AA
4 wt. % AOPA
107 ppm HAc
0.8 ppm toluene

Aqueous distillate (47.8 g/hr):
94.4 wt. % H2O
1.3 wt. % AA
4.3 wt. % HAc
263 ppm toluene The acrylic acid yield loss through the aqueous distillate was 1.24%.

EXAMPLE 3

Azeotropic Distillation with Toluene Solvent at 50% Turndown

An extended azeotropic distillation was run as described in Example 1. The distillation was turndown to run at a 50% turndown rate, i.e., at 50% aqueous feed rate. A calculated amount of aqueous distillate recycle was added to the aqueous feed as make-up water so as to maintain the desired vapor rate.

The operating conditions were as follows:

215 mm Hg top pressure
77.5 g/hr aqueous AA feed rate
24.7 g/hr recycled aqueous distillate feed
300 g/hr toluene reflux rate
70° C. control tray temperature An aqueous acrylic acid feed composition with added recycled aqueous distillate was fed to the distillation column at tray 15 and toluene reflux was fed to the top tray at the rates indicated. The aqueous acrylic acid feed composition contained 67 wt. % acrylic acid, 1 wt. % β-acryloxypropionic acid (AOPA), 28 wt.% water, and 3 wt. % acetic acid, and 1 wt. % other minor components such as formaldehyde, formic acid, maleic acid, and hydroquinone polymerization inhibitor. The hydroquinone was available from Aldrich Chemical Co. of Milwaukee, Wis. Also, 4-hydroxy-2,2,6,6-tetramethylpiperidinyloxy, free radical polymerization inhibitor, available from Aldrich Chemical Co. of Milwaukee, Wis., was fed as a 0.13 wt. % aqueous solution into the aqueous acrylic acid feed at a rate of 5 g/hr and p-benzoquinone vapor phase inhibitor, available from Aldrich Chemical Co. of Milwaukee, Wis., as a 0.12 wt. % toluene solution and an additional stream of 4-hydroxy-2,2,6,6-tetramethylpiperidinyloxy, free radical as a 0.26 wt. % toluene solution were fed to the top tray at a rate of 10 g/hr. The inhibitor feeds resulted in inhibitor levels in the column, based on bottoms, of 200 ppm of 4-hydroxy-2,2,6,6-tetramethyl piperidinyloxy, free radical, 316 ppm hydroquinone, and 650 ppm of p-benzoquinone.

The experiment ran smoothly for 20 hours. At the end of the run, the column and pot were clean and the effluent streams had the following compositions:

Bottoms (53.5 g/hr):
96 wt. % AA
4 wt. % AOPA
360 ppm HAc
1.1 ppm toluene

Aqueous distillate (24.7 g/hr recycled, 24.0 g/hr waste):
91.2 wt. % H2O
1.2 wt. % AA
7.6 wt. % HAc
295 ppm toluene The acrylic acid yield loss through the aqueous distillate was 0.53%.

Examples 1, 2 and 3 showed maintenance of distillation column performance, including good separation characteristics, even at turndown utilizing DI water (Example 2) and at turndown using recycled aqueous distillate (Example 3). Such maintenance of column performance is evidenced by equivalent recovery of acrylic acid in the distillation column bottoms, i.e., 96 weight % acrylic acid, despite turndown of the aqueous acrylic acid feed. Also, as seen in Example 3, utilization of the aqueous distillate from the distillation column overhead to adjust the water fed to the distillation column to compensate for turndown of the aqueous acrylic acid feed reduces the wastewater load on the system. Furthermore, when Examples 2 and 3 are compared it can be seen that the acrylic acid yield loss in the distillation column overhead is reduced by half, i.e., 1.24% in Example 2 to 0.53% in Example 3 because of the recycle of 50% of the waste water load from the column aqueous distillate to the distillation column.

We claim:

1. A process for preparing (meth)acrylic acid, comprising the steps of:
   (A) feeding an aqueous (meth)acrylic acid stream comprising (meth)acrylic acid to a distillation column;
   (B) distilling the aqueous (meth)acrylic acid stream at a predetermined vapor rate, in the presence of at least one distillation solvent substantially insoluble in water, to form a crude (meth)acrylic acid stream; and
   (C) maintaining the predetermined vapor rate in response to aqueous (meth)acrylic acid fluctuation by
      (i) monitoring a distillation solvent to water ratio during distillation, and
      (ii) adjusting at least one of the amount of water and the amount of distillation solvent fed to the distillation column to maintain the predetermined vapor rate.

2. The process of claim 1, further comprising phase separating overheads from the distillation column into an organic phase and an aqueous phase wherein at least a portion of the organic phase is recycled back to the distillation column.

3. The process of claim 1, wherein the amount of water fed to the column is adjusted using recycled wastewater.

4. The process of claim 1, further comprising phase separating overheads from the distillation column into an organic phase and an aqueous phase, wherein at least a portion of the aqueous phase is used to adjust the water fed to the column.

5. The process of claim 1, wherein the aqueous (meth)acrylic acid stream is stripped of light ends before being fed to the distillation column.

6. The process of claim 1, wherein the at least one distillation solvent substantially insoluble in water is selected from the group consisting of heptane, heptene, cycloheptane, cycloheptene, cycloheptadiene, cycloheptatriene, methylcyclohexane, ethylcyclopentane, dimethylcyclohexane, ethylcyclohexane, toluene, ethylbenzene, xylene, trichloroethylene, trichloropropene, dichlorobutane, chloropentane, chlorohexane, chlorobenzene, and mixtures thereof.

7. The process of claim 1, wherein the at least one distillation solvent substantially insoluble in water is toluene.

8. The process of claim 1, wherein the distillation column is a dual flow tray column.

9. The process of claim 1, wherein at least one polymerization inhibitor selected from the group hydroquinone; 4-methoxyphenol; 4-ethoxyphenol; 1,2-dihydroxybenzene; 2-methoxyphenol; p-benzoquinone; phenothiazine; pyrogallol; t-butyl catechol; 4-aminophenol; 2-aminophenol; di-t-butyl nitroxide; 2,2,6,6-tetramethyl piperidinyloxy, free radical; 4-hydroxy-2,2,6,6-tetramethyl piperidinyloxy, free radical; 4-oxo-2,2,6,6-tetramethylpiperidinyloxy, free radical; 4-amino-2,2,6,6-tetramethylpiperidinyloxy, free radical; 4-ethanoyl-2,2,6,6-tetramethylpiperidinyloxy, free radical;

2,2,5,5-tetramethylpyrrolidinyloxy, free radical; isomers thereof; derivatives thereof; mixtures of two or more thereof; or mixtures of one or more of the above with molecular oxygen is added to the distillation column.

10. The process of claim 8, wherein the dual flow tray column contains trays having weep holes to prevent retention of polymerizable liquid on the trays.

11. A process for preparing (meth)acrylic acid, comprising the steps of:
   (A) feeding an aqueous (meth)acrylic acid stream comprising (meth)acrylic acid and at least one polymerization inhibitor selected from 4-hydroxy-2,2,6,6-tetramethyl-piperidinyloxy and derivatives thereof to a distillation column;
   (B) distilling the aqueous (meth)acrylic acid stream at a predetermined vapor rate, in the presence of at least one distillation solvent, to form a crude (meth)acrylic acid stream; and
   (C) maintaining the predetermined vapor rate in response to aqueous (meth)acrylic acid feed rate fluctuation by
     (i) monitoring a distillation solvent to water ratio, and
     (ii) adjusting at least one of the amount water and the amount of distillation solvent fed to the distillation column to maintain the predetermined vapor rate.

12. The process of claim 11, further comprising phase separating overheads from the distillation column into an organic phase and an aqueous phase wherein at least a portion of the organic phase is recycled back to the distillation column.

13. The process of claim 11, wherein the amount of water fed to the column is adjusted using recycled wastewater.

14. The process of claim 11, further comprising phase separating overheads from the distillation column into an organic phase and an aqueous phase, wherein at least a portion of the aqueous phase is used to adjust the water fed to the column.

15. The process of claim 11, wherein the aqueous (meth) acrylic acid stream is stripped of light ends before being fed to the distillation column.

16. The process of claim 11, wherein the at least one distillation solvent is selected from the group consisting of heptane, heptene, cycloheptane, cycloheptene, cycloheptadiene, cycloheptatriene, methylcyclohexane, ethylcyclopentane, di-methylcyclohexane, ethylcyclohexane, toluene, ethylbenzene, xylene, trichloroethylene, trichloropropene, dichlorobutane, chloropentane, chlorohexane, chlorobenzene, ethyl acetate, butyl acetate, dibutyl ether, ethyl acrylate, methyl methacrylate, ethyl methacrylate, diethyl ketone, methyl propyl ketone, methyl isobutyl ketone, methyl tert-butyl ketone, isopropyl acetate, n-propyl acetate, and mixtures thereof.

17. The process of claim 14, wherein the portion of the aqueous phase used to adjust the water fed to the column is stripped of distillation solvent before being used to adjust the water fed to the column.

18. The process of claim 11, wherein the distillation column is a dual flow tray column.

19. The process of claim 11, wherein at least one polymerization inhibitor selected from the group hydroquinone; para-benzoquinone; phenothiazine. 4-methoxy phenol; 4-ethoxyphenol; 1,2-dihydroxybenzene; catechol monobutyl ether; pyrogallol; 4-aminophenol; 2-mercaptophenol; 4-mercaptophenol; 4-hydroxy-2,2,6,6-tetramethylpiperidinyloxy, free radical; 4-oxo-2,2,6,6-tetramethylpiperidinyloxy, free radical; 4-amino-2,2,6,6-tetramethyl piperidinyloxy, free radical; 4-propoxyphenol; 4-butoxyphenol; 4-heptoxyphenol; hydroquinone monobenzylether; 1,2-dihydroxybenzene; 2-methoxyphenol; 2,5-dichlorhydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 2-aminophenol; 2-N,N-dimethylamino phenol; 4-ethylaminophenol; 2,3-dihydroxyacetophenone; 1,2-dimethylether; 2-methylthiophenol; t-butyl catechol; di-tert-butylnitroxide; di-tert-amylnitroxide; 2,2,6,6-tetramethyl-piperidinyloxy; 4-dimethylamino 2,2,6,6-tetramethylpiperidinyloxy; 4-amino-2,2,6,6-tetramethyl-piperidinyloxy; 4-ethanoyloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; copper compounds such as copper dimethyldithiocarbamate; copper diethyldithiocarbamate; copper salicylate; isomers thereof; derivatives thereof; mixtures of two or more thereof; or mixtures of one or more of the above with molecular oxygen is added to the distillation column.

20. The process of claim 11, wherein the dual flow tray column has trays containing weep holes to prevent retention of polymerizable liquid on the trays.

* * * * *